United States Patent
Lee et al.

(10) Patent No.: US 10,724,111 B2
(45) Date of Patent: Jul. 28, 2020

(54) MOLECULAR DETECTION OF ENTEROVIRUS AND PARECHOVIRUS

(71) Applicant: QUEST DIAGNOSTICS INVESTMENTS LLC, Secaucus, NJ (US)

(72) Inventors: Peter Lee, Tustin, CA (US); Lakshmi Nair, Yorba Linda, CA (US); Albert Castro, Walnut, CA (US); Maria Vestal, Lakewood, CA (US); Michelle Tabb, Santa Ana, CA (US)

(73) Assignee: Quest Diagnostics Investments LLC, Secaucus, NJ (US)

( * ) Notice: Subject to any disclaimer, the term of this patent is extended or adjusted under 35 U.S.C. 154(b) by 0 days.

(21) Appl. No.: 16/436,709

(22) Filed: Jun. 10, 2019

(65) Prior Publication Data

US 2019/0382856 A1 Dec. 19, 2019

Related U.S. Application Data

(62) Division of application No. 16/124,534, filed on Sep. 7, 2018, now Pat. No. 10,316,372, which is a division of application No. 15/305,877, filed as application No. PCT/US2015/027951 on Apr. 28, 2015, now Pat. No. 10,072,308.

(60) Provisional application No. 61/985,223, filed on Apr. 28, 2014.

(51) Int. Cl.
| | | |
|---|---|---|
| C12Q 1/68 | (2018.01) | |
| C12P 19/34 | (2006.01) | |
| C12Q 1/70 | (2006.01) | |
| C07H 21/04 | (2006.01) | |
| C12Q 1/6874 | (2018.01) | |

(52) U.S. Cl.
CPC .................................. C12Q 1/701 (2013.01)

(58) Field of Classification Search
CPC ... C12Q 1/686; C12Q 1/6874; C12Q 2563/159; C12Q 2565/627; C12Q 1/701
See application file for complete search history.

(56) References Cited

U.S. PATENT DOCUMENTS

| | | | |
|---|---|---|---|
| 2005/0239055 A1 | 10/2005 | Mariani | |
| 2009/0226889 A1 | 9/2009 | Chen et al. | |
| 2010/0035230 A1* | 2/2010 | Nix .................. | C12Q 1/701 435/5 |

FOREIGN PATENT DOCUMENTS

| | | | |
|---|---|---|---|
| CN | 103215386 | * | 7/2013 |
| CN | 103215386 A | | 7/2013 |
| EP | 1 746 102 A1 | | 1/2007 |
| EP | 1746102 | * | 1/2007 |
| RU | 2189396 C2 | | 9/2002 |
| WO | WO 2003/064605 A2 | | 8/2003 |
| WO | WO2003064605 | * | 8/2003 |

OTHER PUBLICATIONS

Bennett et al., "Rapid Simultaneous Detection of Enterovirus and Parechovirus RNA's in Clinical Samples by One-Step Real-Time Reverse Transcription-PCR Assay," Journal of Clinical Microbiology, vol. 49, No. 7, pp. 2620-2624, May 2011.
International Search Report dated Sep. 8, 2015 in application No. PCT/US2015/027951.
Kost et al: "Multicenter Beta Trial of the GeneXpert Enterovirus Assay", Journal of Clinical Microbiology, vol. 45, No. 4, Jan. 24, 2007, pp. 1081-1086, XP055425723.
Landry et al., "Real-Time Nucleic Acid Sequence-Based Amplification Using Molecular Beacons for Detection of Enterovirus RNA in Clinical Specimens," Journal of Clinical Microbiology, vol. 43, No. 7, pp. 3136-3139, Jul. 2005.
Mattison et al.: "Analytical Methods for Food and Environmental Viruses", Food and Environmental Virology, vol. 1, No. 3-4, Dec. 27, 2009, pp. 107-122, XP055425455.
Monpoeho S et al: "Quantification of Enterovirus RNA in Sludge Samples Using Single Tube Real-Time RT-PCR", Biotechniques Rapid Dispatches, Informa Healthcare, US, vol. 29, No. 1, Jun. 30, 2000, pp. 88-93, XP009501600.
Shanghai Biological Technology Co., CN 103215386 A, 2013: pdf pp. 1-13.
Supplementary Partial European Search Report dated Nov. 28, 2017 as issued in corresponding European Application No. 15786249.1.

* cited by examiner

*Primary Examiner* — Barry A Chestnut
(74) *Attorney, Agent, or Firm* — Foley & Lardner LLP

(57) ABSTRACT

Provided herein are methods for determining the presence or absence of an enteroviruses and parechoviruses in a biological sample. The methods involve identifying the presence or absence of a target nucleic acids from the viruses using direct amplification from a biological sample without a step of extraction of the nucleic acids, but retaining substantially the same specificity and sensitivity of methods assaying extracted nucleic acids. Also provided are methods of diagnosis using the methods provided and compositions and kits for the practice of the methods.

5 Claims, No Drawings

Specification includes a Sequence Listing.

SEQUENCE LISTING

```
<160> NUMBER OF SEQ ID NOS: 8

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
aattgtcacc ataagcagcc a                                              21

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
cccctgaatg cggctaatc                                                 19

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
acacggacac ccaaagtagt cggt                                           24

<210> SEQ ID NO 4
```

```
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gttgtaaggc ccacgaa                                                       17

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (17)..(17)
<223> OTHER INFORMATION: Inosine

<400> SEQUENCE: 5
tcagatccat agtgtcnctt gtta                                               24

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
atgcccagaa ggtacccg                                                      18

<210> SEQ ID NO 7
<211> LENGTH: 53
<212> TYPE: DNA
<213> ORGANISM: Artificial Sequence
<220> FEATURE:
<223> OTHER INFORMATION: Description of Artificial Sequence: Synthetic
      primer-probe
<220> FEATURE:
<221> NAME/KEY: misc_feature
<222> LOCATION: (34)..(35)
<223> OTHER INFORMATION: Nucleotides at these positions are non-
      consecutive and are separated by a FAM-Spacer18 moiety

<400> SEQUENCE: 7
agcgcacacg gacacccaaa gtagtcggtg cgctcccctg aatgcggcta atc               53

<210> SEQ ID NO 8
<211> LENGTH: 52
<212> TYPE: DNA
<213> ORGANISM: Artificial Sequence
<220> FEATURE:
<223> OTHER INFORMATION: Description of Artificial Sequence: Synthetic
      primer-probe
<220> FEATURE:
<221> NAME/KEY: misc_feature
<222> LOCATION: (28)..(29)
<223> OTHER INFORMATION: Nucleotides at these positions are non-
      consecutive and are separated by a BHQ-2-Spacer18 moiety
<220> FEATURE:
<221> NAME/KEY: modified_base
<222> LOCATION: (45)..(45)
<223> OTHER INFORMATION: Inosine

<400> SEQUENCE: 8
cgcgcgatgc ccagaaggta cccgcgcgtc agatccatag tgtcncttgt ta                52
```

MOLECULAR DETECTION OF ENTEROVIRUS AND PARECHOVIRUS

CROSS-REFERENCE TO RELATED APPLICATIONS

This application is a Divisional of U.S. application Ser. No. 16/124,534, filed Sep. 7, 2018, which is a Divisional of U.S. application Ser. No. 15/305,877, which is the U.S. National Stage application of PCT/US2015/027951, filed Apr. 28, 2015, which claims priority from U.S. Provisional Application No. 61/985,223, filed Apr. 28, 2014.

SEQUENCE LISTING

The instant application contains a Sequence Listing which has been submitted electronically in ASCII format and is hereby incorporated by reference in its entirety. Said ASCII copy, created on Sep. 5, 2018, is named sequence.txt and is 3 KB in size.

FIELD OF THE INVENTION

The present invention relates to methods for detecting and differentiating enterovirus and parechovirus in biological samples.

BACKGROUND OF THE INVENTION

The following discussion of the background of the invention is merely provided to aid the reader in understanding the invention and is not admitted to describe or constitute prior art to the present invention.

Enteroviruses belong to the Picornaviridae family of viruses. They are transmitted from person to person via direct contact with virus shed from the gastrointestinal or upper respiratory tract, affecting millions of people worldwide each year. They are often found in respiratory secretions, e.g., saliva, sputum, or nasal mucus, stool, and cerebrospinal fluid of an infected person. Enteroviral infection can result in a wide variety of symptoms ranging from mild respiratory illness (common cold), hand, foot and mouth disease, acute hemorrhagic conjunctivitis, aseptic meningitis, myocarditis, severe neonatal sepsis-like disease, and acute flaccid paralysis. Historically, poliomyelitis was the most significant disease caused by an enterovirus, poliovirus. However, there are additionally at least 62 non-polio enteroviruses that can cause disease in humans, including Coxsackie A viruses, Coxsackie B viruses, and echoviruses.

Parechovirus is a viral genus in the family Picornaviridae, a large family of non-enveloped, positive-sense, single-stranded RNA viruses that have an icosahedral capsid. The capsid is an arrangement of 60 protomers, each formed from 4 proteins (VP1 to VP4), and encloses the linear RNA genome. The parechovirus genus is composed of two species: Human parechovirus and Ljungan virus. Human parechoviruses are commonly spread and cause mild, gastrointestinal or respiratory illness, but have been implicated in cases of myocarditis and encephalitis. More than 95% of humans are infected by human parechovirus early in life, within two to five years of age.

Clinical detection of viruses is usually accomplished using any one of a variety of methods. For example, virus particles or nucleic acids may be isolated from a biological sample (e.g., cerebrospinal fluid, nasopharyngeal aspirates, throat swabs, blood fluids, fecal material, urine, etc.). A retrospective diagnosis may be made by serology. Complement Fixation Tests (CFT) are most widely used in this method, although hemagglutination inhibition (HAI) and enzyme immunoassays (EIA) may be used to give a type-specific diagnosis. For more rapid diagnosis, either antigen detection or RNA detection may be performed. However, screening for multiple antigens or nucleotide sequences may be necessary because of the large number of viruses in these families. In addition, nucleic acids usually must be extracted from a crude biological sample in order to accurately detect the presence of nucleic acids from microorganisms.

Given the high degree of complexity associated with preparing and processing viral nucleic acids from biological samples for detection, diagnosis, and/or quantitation in cases where rapid diagnosis is sought, there is a need for methods involving fewer steps, fewer technological requirements, and shorter durations. In addition, there exists a further need for methods that can detect and differentiate the multiple types of enterovirus and parechovirus from other viruses in human samples with the fewest number of steps and without the need to extract nucleic acids from the samples.

SUMMARY OF THE INVENTION

Provided herein are methods for determining the presence or absence of an enterovirus and/or a parechovirus in a biological sample.

In one aspect, the present invention provides a method for determining the presence or absence of an enterovirus in a sample, the method comprising amplifying enteroviral nucleic acids, if present in the sample, with at least one pair of primers, wherein a first primer of the pair has a primer element that specifically hybridizes under stringent conditions to a nucleic acid comprising or consisting of SEQ ID NO:1 or the full complement thereof, and a second primer of the pair has a primer element that specifically hybridizes under stringent conditions to a nucleic acid comprising or consisting of SEQ ID NO:2 or the full complement thereof.

In some embodiments, the method for determining the presence or absence of an enterovirus in a sample includes (a) heating a biological sample to a first predetermined temperature for a first predetermined time to separate the secondary structure of RNA present in the sample, (b) contacting the sample with a reaction mix to form a reaction mixture, wherein the reaction mix comprises a pair of primers, a DNA polymerase, a reverse transcriptase, and a plurality of free nucleotides comprising adenine, thymine, cytosine and guanine, wherein one primer of the pair has a primer element that specifically hybridizes under stringent conditions to a nucleic acid comprising or consisting of SEQ ID NO:1 or the full complement thereof, and the other primer of the pair has a primer element that specifically hybridizes under stringent conditions to a nucleic acid comprising or consisting of SEQ ID NO:2 or the full complement thereof, (c) cooling the reaction mixture to a second predetermined temperature for a second predetermined time under conditions to allow the reverse transcription of the RNA, (d) amplifying a target nucleic acid sequence, wherein amplification comprises a step of cooling the reaction mixture to a third predetermined temperature for a third predetermined time under conditions to allow the primer element of the primers to hybridize with their complementary sequences, if present, on the first and second strands of cDNA, and to allow the DNA polymerase to extend the primers, and (e) repeating step (d). An enterovirus is determined to be present in the sample if an enteroviral target sequence is amplified to produce an amplicon in the reaction mixture. In some embodiments, step (a) is performed prior to step (b) (e.g., the biological sample is heated, and the heated sample is contacted with the reaction mix to form the reaction mixture). In some embodiments, step (b) is performed prior to step (a) (e.g., the biological sample is contacted with the reaction mix to form the reaction mixture, and then the reaction mixture containing the biological sample is heated).

In some embodiments, the first primer of the pair for detection of an enterovirus has a primer element that is at least 90% identical to SEQ ID NO:1 or the full complement of SEQ ID NO:1 and a detectable label that is not a nucleic acid. In some embodiments, the first primer is a primer-probe. In some embodiments, the primer-probe has a probe element comprising a nucleotide sequence at least 90% identical to SEQ ID NO:3 or the full complement of SEQ ID NO:3. The probe element may further comprise a quencher, a fluorophore, and two self-complementary stem sequences wherein each stem sequence is at least 4, 5, 6 or 7 nucleotides in length. In addition, the second primer of the pair may have a primer element comprising a nucleotide sequence that is at least 90% identical to SEQ ID NO:2 or the full complement of SEQ ID NO:2.

In some embodiments, the first primer of the pair for detection of an enterovirus has a primer element comprising a nucleotide sequence that is at least 90% identical to SEQ ID NO:2 or the full complement of SEQ ID NO:2 and a detectable label that is not a nucleic acid. In some embodiments, the first primer is a primer-probe. In some embodiments, the primer-probe has a probe element that comprises a nucleotide sequence at least 90% identical to SEQ ID NO:3 or the full complement of SEQ ID NO:3. In some embodiments, the probe element further comprises a quencher, a fluorophore, and two self-complementary stem sequences wherein each stem sequence is at least 4, 5, 6 or 7 nucleotides in length. In some embodiments, the second primer of the pair may have a primer element at least 90% identical to SEQ ID NO:1 or the full complement of SEQ ID NO:1.

Another aspect of the present invention provides a method for determining the presence or absence of parechovirus in a sample, the method comprising amplifying parechoviral nucleic acids, if present in the sample, with at least one pair of primers, wherein a first primer of the pair has a primer element that specifically hybridizes under stringent conditions to a nucleic acid comprising or consisting of SEQ ID NO:4 or the full complement thereof, and a second primer of the pair has a primer element that specifically hybridizes under stringent conditions to a nucleic acid comprising or consisting of SEQ ID NO: 5 or the full complement thereof.

In some embodiments, the method for determining the presence or absence of a parechovirus in a sample includes (a) heating a biological sample to a first predetermined temperature for a first predetermined time to separate the secondary structure of RNA present in the sample, providing a reaction mixture comprising a sample, a pair of primers, a DNA polymerase, (b) contacting the sample with a reaction mix to form a reaction mixture, wherein the reaction mix comprises a pair of primers, a DNA polymerase, a reverse transcriptase, and a plurality of free nucleotides comprising adenine, thymine, cytosine and guanine, wherein one primer of the pair has a primer element that specifically hybridizes under stringent conditions to a nucleic acid comprising or consisting of SEQ ID NO:4 or the full complement thereof, and the other primer of the pair has a primer element that specifically hybridizes to a nucleic acid comprising or consisting of SEQ ID NO: 5 or the full complement thereof, (c) cooling the reaction mixture to a second predetermined temperature for a second predetermined time under conditions to allow the reverse-transcription of the RNA, (d) amplifying a target nucleic acid sequence, wherein amplification comprises a step of cooling the reaction mixture to a third predetermined temperature for a third predetermined time under conditions to allow the primer element of the primers to hybridize with their complementary sequences, if present, on the first and second strands of cDNA, and to allow the DNA polymerase to extend the primers, (e) repeating step (d). A parechovirus is determined to be present in the sample if an parechoviral target sequence is amplified to produce an amplicon in the reaction mixture. In some embodiments, step (a) is performed prior to step (b) (e.g., the biological sample is heated, and the heated sample is contacted with the reaction mix to form the reaction mixture). In some embodiments, step (b) is performed prior to step (a) (e.g., the biological sample is contacted with the reaction mix to form the reaction mixture, and then the reaction mixture containing the biological sample is heated).

In some embodiments, the first primer of the pair for detection of a parechovirus has a primer element comprising a nucleotide sequence that is at least 90% identical to SEQ ID NO:4 or the full complement of SEQ ID NO:4, and a detectable label that is not a nucleic acid. In some embodiments, the first primer is a primer-probe. In some embodiments, the primer-probe has a probe element that comprises a nucleotide sequence at least 90% identical to SEQ ID NO:6 or the full complement of SEQ ID NO:6. In some embodiments, the probe element further comprises a quencher, a fluorophore, and two self-complementary stem sequences wherein each stem sequence is at least 4, 5, 6 or 7 nucleotides in length. In addition, in some embodiments the second primer of the pair has a primer element comprising a nucleotide sequence that is at least 90% identical SEQ ID NO:5 or the full complement of SEQ ID NO:5.

In some embodiments, the first primer of the pair for detection of a parechovirus has a primer element that is at least 90% identical to SEQ ID NO:5 or the full complement of SEQ ID NO:5 and a detectable label that is not a nucleic acid. In some embodiments, the first primer is a primer-probe. In some embodiments, the primer-probe has a probe element comprising a nucleotide sequence at least 90% identical to SEQ ID NO:6 or the full complement of SEQ ID NO:6. The probe element may further comprise a quencher, a fluorophore, and two self-complementary stem sequences wherein each stem sequence is at least 4, 5, 6 or 7 nucleotides in length. In addition, the second primer of the pair may have a primer element comprising a nucleotide sequence that is at least 90% identical to SEQ ID NO:4 or the full complement of SEQ ID NO:4.

In some embodiments, the disclosed methods are used to determine the presence or absence of an enterovirus and a parechovirus in a sample that is a biological sample selected from the group consisting of cerebrospinal fluid, blood, stool, throat swab, rectal swab, nasopharynx swab, plasma, serum and urine. In some embodiments, nucleic acids are not extracted from the biological sample prior to reverse transcription or amplification. In some embodiments, the sample contains cDNA reverse transcribed from RNA. In some embodiments, the sample comprises RNA, the reaction mixture further comprises a reverse transcriptase, and the reaction mixture is heated to a predetermined temperature for a predetermined time to separate the secondary structure of RNA present in the sample and then cooled to reverse transcribe RNA in the sample into cDNA in the presence of a reverse transcriptase.

Another aspect of the invention provides a method for detecting the presence or absence of an enterovirus and a parechovirus in a sample includes (a) heating a biological sample to a first predetermined temperature for a first predetermined time to separate the secondary structure of RNA present in the sample, (b) contacting the sample with a reaction mix to form a reaction mixture, wherein the reaction mix comprises a first and second pair of primers, a DNA polymerase, a reverse transcriptase, and a plurality of free nucleotides comprising adenine, thymine, cytosine and guanine, wherein one primer of the first primer pair has a primer element that specifically hybridizes under stringent conditions to a nucleic acid comprising or consisting of SEQ ID NO:1 or the full complement thereof, and the other primer of the first primer pair has a primer element that specifically hybridizes under stringent conditions to a nucleic acid comprising or consisting of SEQ ID NO:2 or the full complement thereof, and wherein one primer of the second primer pair has a primer element that specifically hybridizes to a nucleic acid comprising or consisting of SEQ ID NO:4 or the full complement thereof, and the other primer of the second primer pair has a primer element that specifically hybridizes to a nucleic acid comprising or consisting of SEQ ID NO: 5 or the full complement thereof, (c) cooling the reaction mixture to a second predetermined temperature for a second predetermined time under conditions to allow the reverse-transcription of the RNA, (d) amplifying a target nucleic acid sequence, wherein amplification comprises a step of cooling the reaction mixture to a third predetermined temperature for a third predetermined time under conditions to allow the primer element of the primers to hybridize with their complementary sequences, if present, on the first and second strands of cDNA, and to allow the DNA polymerase to extend the primers, and (e) repeating step (d). An enterovirus is determined to be present in the sample if an enteroviral target sequence is amplified to produce an amplicon in the reaction mixture and a parechovirus is determined to be present in the sample if a parechovirus target sequence is amplified to produce an amplicon in the reaction mixture. In some embodiments, step (a) is performed prior to step (b) (e.g., the biological sample is heated, and the heated sample is contacted with the reaction mix to form the reaction mixture). In some embodiments, step (b) is performed prior to step (a) (e.g., the biological sample is contacted with the reaction mix to form the reaction mixture, and then the reaction mixture containing the biological sample is heated).

Another aspect of the invention provides a composition comprising a primer with a primer element that is at least 90% identical to a sequence selected from the group consisting of SEQ ID NO:1, the full complement of SEQ ID NO:1, SEQ ID NO:2, the full complement of SEQ ID NO:2, SEQ ID NO:4, the full complement of SEQ ID NO:4, SEQ ID NO:5 and the full complement of SEQ ID NO:5. In some embodiments, the primer is linked directly or indirectly to a detectable label. The composition may be a primer-probe, further comprising a probe element linked directly or indirectly to the primer element by a polymerase-blocking group wherein the probe element comprises a nucleic acid sequence at least 90% identical to SEQ ID NO:3, the full complement of SEQ ID NO:3, SEQ ID NO:6 or the full complement of SEQ ID NO:6. In some embodiments, the primer-probe further comprises a quencher dye, and the detectable label is a fluorophore.

In a specific embodiment, a primer-probe comprises a 5' quencher dye, SEQ ID NO:3 flanked by two self-complementary nucleotide sequences at least 4 nucleotides in length, a fluorophore and/or a nucleic acid comprising SEQ ID NO:2. In another specific embodiment, a primer-probe comprises a 5' fluorophore, a nucleic acid comprising SEQ ID NO:6 flanked by two self-complementary nucleotide sequences at least 4 nucleotides in length, a quencher dye, and a nucleic acid comprising SEQ ID NO:5. In some embodiments, the primer-probe further comprises a spacer consisting of polyethylene glycol. In some embodiments, the spacer comprises an 18-atom polyethylene glycol-based linker. In some embodiments, the spacer consists of material other than nucleotides (i.e. a non-nucleotide spacer). In some embodiments, the spacer may be located immediately 5' of the primer element.

The present invention also provides kits comprising the oligonucleotides, primers and primer-probes disclosed herein. In one embodiment, a kit comprises a first primer having a primer element that specifically hybridizes to a nucleic acid comprising or consisting of SEQ ID NO:1 or the full complement thereof, and a second primer having a primer element that specifically hybridizes to a nucleic acid comprising or consisting of SEQ ID NO:2 or the full complement thereof, wherein at least one of the primers is labeled with a detectable label that is not a nucleic acid. In one embodiment, a kit comprises a first primer having a primer element that specifically hybridizes to a nucleic acid comprising or consisting of SEQ ID NO:4 or the full complement thereof, and a second primer having a primer element that specifically hybridizes to a nucleic acid comprising or consisting of SEQ ID NO:5 or the full complement thereof, wherein at least one of the primers is labeled with a detectable label that is not a nucleic acid.

In one embodiment, a kit comprises (a) a first primer pair comprising a first primer having a primer element that specifically hybridizes to a nucleic acid comprising or consisting of SEQ ID NO:1 or the full complement thereof, and a second primer having a primer element that specifically hybridizes to a nucleic acid comprising or consisting of SEQ ID NO:2 or the full complement thereof; and (b) a second primer pair comprising a first primer having a primer element that specifically hybridizes to a nucleic acid comprising or consisting of SEQ ID NO:3 or the full complement thereof, and a second primer having a primer element that specifically hybridizes to a nucleic acid comprising or consisting of SEQ ID NO:5 or the full complement thereof wherein at least one of the primers of the first and second primer pair is labeled with a detectable label that is not a nucleic acid.

In one embodiment provided is a kit comprising a primer pair that detects an enterovirus and a primer pair that detects a parechovirus as described herein. Another embodiment provides a kit comprising a primer pair that detects at least 64 serotypes of enterovirus and a primer pair that detects at least 8 serotypes of parechovirus.

Another aspect of the invention provides a method of amplifying a target nucleotide sequence comprising providing a reaction mixture comprising a double stranded target DNA, a pair of primers wherein the first primer specifically hybridizes to a nucleic acid comprising or consisting of SEQ ID NO:1 or the full complement thereof, and the second primer specifically hybridizes to a nucleic acid comprising or consisting of SEQ ID NO:2 or the full complement thereof, a DNA polymerase, and a plurality of free nucleotides comprising adenine, thymine, cytosine and guanine; heating the reaction mixture to a first predetermined temperature for a first predetermined time to separate the strands of the double stranded DNA from each other, cooling the reaction mixture to a second predetermined temperature for a second predetermined time under conditions to allow the first and second primers to hybridize with their complementary sequences on the first and second strands of the target DNA, and to allow the DNA polymerase to extend the primers, and repeating steps above. In some embodiments, at least one of the primers is primer-probe comprising a detectable label that is not a nucleic acid. In some embodiments, the primers are primers as disclosed herein. In some embodiments, the DNA is a cDNA.

Another aspect of the invention provides a method of amplifying a target nucleotide sequence comprising providing a reaction mixture comprising a double stranded target DNA, a pair of primers wherein the first primer specifically hybridizes to a nucleic acid comprising or consisting of SEQ ID NO:4 or the full complement thereof, and the second primer specifically hybridizes to a nucleic acid comprising or consisting of SEQ ID NO: 5 or the full complement thereof, a DNA polymerase, and a plurality of free nucleotides comprising adenine, thymine, cytosine and guanine; heating the reaction mixture to a first predetermined temperature for a first predetermined time to separate the strands of the double stranded DNA from each other, cooling the reaction mixture to a second predetermined temperature for a second predetermined time under conditions to allow the first and second primers to hybridize with their complementary sequences on the first and second strands of the target DNA, and to allow the DNA polymerase to extend the primers, and repeating steps above. In some embodiments, at least one of the primers is primer-probe comprising a detectable label that is not a nucleic acid. In some embodiments, the primers are primers as disclosed herein. In some embodiments, the DNA is a cDNA.

The methods disclosed herein additionally can be used to diagnose an individual as infected with enterovirus or parechovirus.

DETAILED DESCRIPTION

The present invention is directed to diagnostic methods for the detection of enterovirus and parechovirus using a multiplex analyte detection system. The method does not require an extraction or purification step to isolate viral (i.e., target) nucleic acid prior to PCR. The disclosed methods can detect 64 serotypes of enterovirus and parechovirus serotypes 1-8 in an unextracted human biological sample.

More particularly, the disclosed sample-to-answer assay is designed as a moderate complexity, multiplex analyte detection system wherein initial sample preparation is followed by reverse transcription and real-time polymerase chain reaction (PCR) detection and differentiation of target enteroviral and parechoviral analytes. In some embodiments, both the reverse transcription and real-time PCR are performed in a centrifugal microfluidic disc such as a consumable Universal or Direct Amplification Disc (Focus Diagnostics (Cypress, Calif., USA) and 3M Company (St. Paul, Minn., USA)). In such embodiments, a biological sample is loaded directly into the sample-to-answer disc, without requiring a separate front-end sample preparation. Qualitative detection and differentiation of enterovirus and parechovirus then utilizes primer-probes such as SCORPION® chemistry primers and real-time PCR for amplification and detection of target analytes on a cycler system such as the 3M Integrated Cycler system. In some embodiments, target viral genomic RNA is reverse transcribed and specifically amplified and simultaneously detected by fluorescent-labeled probes in the same reaction well. The presence of each pathogen is determined by a distinct corresponding fluorescent signal. In some embodiments RNA in the sample is reverse transcribed in a first reaction which may or may not be performed in a consumable disc, and the real-time PCR is performed in a separate assay.

Primers, probes, and/or primer-probes specific for amplification and detection of an internal control may be included in the same reaction mix to monitor potential inhibition of PCR. Reagents necessary for target and RNA internal control amplification and detection may be formulated as an all-in-one reaction mix, which is provided as single reaction aliquots.

As used herein, unless otherwise stated, the singular forms "a," "an," and "the" include plural reference. Thus, for example, a reference to "an oligonucleotide" includes a plurality of oligonucleotide molecules, and a reference to "a nucleic acid" is a reference to one or more nucleic acids.

As used herein, "about" means plus or minus 10%.

A primer pair that "specifically hybridizes under stringent conditions" to a target gene need not hybridize to the entire gene. Accordingly, a primer pair may amplify an entire gene amplified or only a segment of a gene, depending on the portion of the gene to which the primers specifically hybridize.

The term "amplification" or "amplify" as used herein includes methods for copying a target nucleic acid, thereby increasing the number of copies of a selected nucleic acid sequence. Amplification may be exponential or linear. A target nucleic acid may be DNA (such as, for example, genomic DNA and cDNA) or RNA. The sequences amplified in this manner form an "amplicon." While the exemplary methods described hereinafter relate to amplification using the polymerase chain reaction (PCR), numerous other methods are known in the art for amplification of nucleic acids (e.g., isothermal methods, rolling circle methods, etc.). The skilled artisan will understand that these other methods may be used either in place of, or together with, PCR methods. See, e.g., Saiki, "Amplification of Genomic DNA" in PCR Protocols, Innis et al., Eds., Academic Press, San Diego, Calif. 1990, pp 13-20; Wharam, et al., Nucleic Acids Res. 2001 Jun. 1; 29(11):E54-E54; Hafner, et al., Biotechniques 2001 April; 30(4):852-860.

The terms "complement," "complementary," or "complementarity" as used herein with reference to polynucleotides (i.e., a sequence of nucleotides such as an oligonucleotide or a target nucleic acid) refer to standard Watson/Crick pairing rules. The complement of a nucleic acid sequence such that the 5' end of one sequence is paired with the 3' end of the other, is in "antiparallel association." For example, the sequence "5'-A-G-T-3'" is complementary to the sequence "3'-T-C-A-5'." Certain bases not commonly found in natural nucleic acids may be included in the nucleic acids described herein; these include, for example, inosine, 7-deazaguanine, Locked Nucleic Acids (LNA), and Peptide Nucleic Acids (PNA). Complementarity need not be perfect; stable duplexes may contain mismatched base pairs, degenerative, or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs. A complement sequence can also be a sequence of RNA complementary to the DNA sequence or its complement sequence, and can also be a cDNA. The term "substantially complementary" as used herein means that two sequences specifically hybridize (defined below). The skilled artisan will understand that substantially complementary sequences need not hybridize along their entire length. A nucleic acid that is the "full complement" or that is "fully complementary" to a reference sequence consists of a nucleotide sequence that is 100% complementary (under Watson/Crick pairing rules) to the reference sequence along the entire length of the nucleic acid that is the full complement. A full complement contains no mismatches to the reference sequence.

As used herein, the term "detecting" used in context of detecting a signal from a detectable label to indicate the presence of a target nucleic acid in the sample does not require the method to provide 100% sensitivity and/or 100% specificity. As is well known, "sensitivity" is the probability that a test is positive, given that the person has a target nucleic acid, while "specificity" is the probability that a test is negative, given that the person does not have the target nucleic acid. A sensitivity of at least 50% is preferred, although sensitivity of at least 60%, at least 70%, at least 80%, at least 90% and at least 99% are clearly more preferred. A specificity of at least 50% is preferred, although specificity of at least 60%, at least 70%, at least 80%, at least 90% and at least 99% are clearly more preferred. Detecting also encompasses assays with false positives and false negatives. False negative rates may be 1%, 5%, 10%, 15%, 20% or even higher. False positive rates may be 1%, 5%, 10%, 15%, 20% or even higher.

A "fragment" in the context of a nucleic acid refers to a sequence of nucleotide residues which are at least about 5 nucleotides, at least about 7 nucleotides, at least about 9 nucleotides, at least about 11 nucleotides, or at least about 17 nucleotides. The fragment is typically less than about 300 nucleotides, less than about 100 nucleotides, less than about 75 nucleotides, less than about 50 nucleotides, or less than 30 nucleotides. In certain embodiments, the fragments can be used in polymerase chain reaction (PCR), various hybridization procedures or microarray procedures to identify or amplify identical or related parts of RNA or DNA molecules. A fragment or segment may uniquely identify each polynucleotide sequence of the present invention.

As used herein, a "kit" refers to a packaged collection of components used for a specific purpose. Non-limiting examples of materials in which a kit may be packaged include boxes, bags, envelopes and tubes, but kit components may be supplied to a consumer in additional types of packaging materials. In some embodiments, the primers and/or probes included in a kit are isolated polynucleotides and may be supplied in tubes, vials or other types of containers within the kit. In some embodiments a kit further contains instructions for using the kit components. The instructions may be printed on a material within the kit or supplied in electronic format. In some embodiments, the printed instructions specify how to use the reagents contained in the kit to detect the presence or absence of an enterovirus and/or parechovirus in a sample.

The term "multiplex PCR" as used herein refers to simultaneous amplification of two or more products within the same reaction vessel. Each product is primed using a distinct primer pair. A multiplex reaction may further include specific probes for each product that are labeled with detectable moieties. In some embodiments, a multiplex PCR reaction employs a primer pair in which one primer is a primer-probe such as, for example, a SCORPION® primer.

As used herein, the term "oligonucleotide" refers to a short polymer composed of deoxyribonucleotides, ribonucleotides or any combination thereof. Oligonucleotides are generally at least about 10, 11, 12, 13, 14, 15, 20, 25, 40 or 50 up to about 100, 110, 150 or 200 nucleotides (nt) in length, more preferably from about 10, 11, 12, 13, 14, or 15 up to about 70 or 85 nt, and most preferably from about 18 up to about 26 nt in length. The single letter code for nucleotides is as described in the U.S. Patent Office Manual of Patent Examining Procedure, section 2422, table 1. In this regard, the nucleotide designation "R" means purine such as guanine or adenine, "Y" means pyrimidine such as cytosine or thymidine (uracil if RNA); and "M" means adenine or cytosine. An oligonucleotide may be used as a primer or as a probe.

As used herein, a "primer" for amplification comprises a primer element wherein the primer element is an oligonucleotide that is complementary to and hybridizes to a target nucleotide sequence and leads to addition of nucleotides to the 3' end of the primer in the presence of a DNA or RNA polymerase. In some embodiments a primer consists of a primer element. However, a primer as used herein may contain additional elements besides the primer element. For example, a primer may contain a primer element and a detectable label such as a fluorophore. Furthermore, a primer may contain a probe element in addition to a primer element. As used herein, the entire molecule is referred to as a primer. A primer-probe is an exemplary primer. The 3' nucleotide of the primer element in a primer should generally be identical to the target nucleic acid sequence at a corresponding nucleotide position for optimal expression and amplification. The term "primer" as used herein includes all forms of primers that may be synthesized including peptide nucleic acid primers, locked nucleic acid primers, phosphorothioate modified primers, labeled primers, and the like. As used herein, a "forward primer" has a primer element that is complementary to the anti-sense strand of dsDNA. A "reverse primer" has a primer element that is complementary to the sense-strand of dsDNA. An "exogenous primer" refers specifically to a primer that is added to a reaction vessel containing a sample and/or target nucleic acid to be amplified (i.e., is not produced from amplification in the reaction vessel).

A primer element in a primer is typically from at least 10, 12, 15, 18, or 30 nucleotides in length up to about 25, 50, 60, 100, 110, 125, or 200 nucleotides in length, preferably from at least 15 up to about 60 nucleotides in length, and most preferably from at least 25 up to about 40 nucleotides in length. In some embodiments, a primer, a primer element, or a probe is 15 to 35 nucleotides in length. There is no standard length for optimal hybridization or polymerase chain reaction amplification. An optimal length for a particular primer application may be readily determined in the manner described in H. Erlich, PCR Technology, Principles and Application for DNA Amplification, (1989). A primer element may be linked directly or indirectly to another constituent such as, for example, a probe element and/or a fluorophore. Indirect linkage means that the two components are connected through one or more additional components that reside in between the two indirectly linked components. Two components are directly linked when they are connected to each other directly with no intervening components.

A "primer pair" is a pair of primers with primer elements that are both directed to different regions of a target nucleic acid sequence. A primer pair contains a forward primer and a reverse primer, each of which has a primer element that hybridizes under stringent condition to a different strand of a double-stranded target nucleic acid sequence. The forward primer element is complementary to the anti-sense strand of the dsDNA and the reverse primer element is complementary to the sense strand. One primer of a primer pair may be a primer-probe (i.e., a bi-functional molecule that contains a PCR primer element covalently linked by a polymerase-blocking group to a probe element and, in addition, may contain a fluorophore that interacts with a quencher).

A "probe" as used herein is an oligonucleotide that specifically hybridizes to a target nucleotide sequence and is separate from a primer element. A probe sequence is not extended like a primer element and a probe as used herein, unlike a "probe element," does not comprise a primer sequence element. However, a probe may contain additional non-hybridizing elements such as, for example, additional nucleotides or a fluorophore. A TaqMan® probe is an exemplary probe. A TaqMan® probe comprises a donor and a quencher fluorophore on either end of the probe and in close enough proximity to each other so that the fluorescence of the donor is taken up by the quencher. However, when the probe hybridizes to the amplified segment, the 5' to 3' exonuclease activity of the Taq polymerase cleaves the probe thereby allowing the donor fluorophore to emit fluorescence which can be detected.

As used herein "TaqMan® PCR detection system" refers to a method for real-time PCR. In this method, a TaqMan® probe which hybridizes to the nucleic acid segment amplified is included in the amplification master mix.

A "probe element" or "probe sequence element" as used herein refers to a probe portion of a primer-probe and is a stretch of nucleotides that is associated with a primer sequence in that it is connected to or adjacent to the primer nucleic acid sequence, and that specifically hybridizes under stringent conditions to a target nucleic acid sequence to be detected. In some embodiments, a probe sequence is fully complementary to a target sequence to which it is intended to hybridize under stringent conditions. In some embodiments, a probe element is 10, 15, 20, 21, 22, 23, 24, 25, 26, 27, or 28 bases long. In some embodiments, a probe element further comprises self-complementary stem sequences.

As used herein, the term "primer-probe" is a bi-functional molecule such as, for example a SCORPION® primer, that contains a PCR primer element covalently linked at its 5' end by a polymerase-blocking group to a probe element. The probe element comprises a probe target sequence (that specifically binds to the amplified product)—flanked by self-complementary stem sequences and is capable of forming a hairpin structure with a fluorophore at one end and a quencher at the other. At times, the fluorophore interacts with the quencher to reduce the background fluorescence. The primer sequence portion of the primer-probe is modified at the 5' end so as to contain a PCR blocker at the start of the hairpin loop (usually HEG monomers are added as blocking agent).

In the initial PCR cycles, the primer portion of the primer-probe hybridizes to the target and extension occurs due to the action of polymerase. During PCR, the polymerase is blocked from extending into the probe tail by the inclusion of hexaethylene glycol (HEG) or an equivalent substance. During the first round of amplification the 3' target-specific primer anneals to the target nucleic acid and is extended such that the primer-probe is now incorporated into the newly synthesized strand, which possesses a newly synthesized target region for the 5' probe. During the next round of denaturation and annealing, the probe region of the primer-probe hairpin loop hybridizes to the target, thus separating the fluorophore and quencher and creating a measurable signal. Such primer-probes are described in Whitcombe et al., Nature Biotech 17: 804-807 (1999), incorporated by reference herein in its entirety.

As used herein, a "primer-probe detection system" refers to a system for real-time PCR that employs primers wherein at least one primer of a primer pair is a primer-probe such as, for example, a SCORPION® primer.

An oligonucleotide (e.g., a probe or a primer) that is specific for a target nucleic acid will "hybridize" to the target nucleic acid under stringent conditions. As used herein, "hybridization" or "hybridizing" refers to the process by which an oligonucleotide single strand anneals with a complementary strand through base pairing under defined hybridization conditions.

"Specific hybridization" is an indication that two nucleic acid sequences share a high degree of complementarity. Specific hybridization complexes form under permissive annealing conditions and remain hybridized after any subsequent washing steps. Permissive conditions for annealing of nucleic acid sequences are routinely determinable by one of ordinary skill in the art and may occur, for example, at 65° C. in the presence of about 6×SSC. Stringency of hybridization may be expressed, in part, with reference to the temperature under which the wash steps are carried out. Such temperatures are typically selected to be about 5° C. to 20° C. lower than the thermal melting point (Tm) for the specific sequence at a defined ionic strength and pH. The Tm is the temperature (under defined ionic strength and pH) at which 50% of the target nucleic acid dissociates from a perfectly matched probe. Equations for calculating Tm and conditions for nucleic acid hybridization are known in the art. Specific hybridization preferably occurs under stringent conditions, which are well known in the art. Stringent hybridization conditions are hybridization in 50% formamide, 1 M NaCl, 1% SDS at 37° C., and a wash in 0.1×SSC at 60° C. Hybridization procedures are well known in the art and are described in e.g. Ausubel et al, Current Protocols in Molecular Biology, John Wiley & Sons Inc., 1994.

As used herein, an oligonucleotide is "specific" for a nucleic acid if the oligonucleotide has at least 50% sequence identity with the nucleic acid when the oligonucleotide and the nucleic acid are aligned. An oligonucleotide that is specific for a nucleic acid is one that, under the appropriate hybridization or washing conditions, is capable of hybridizing to the target of interest and not substantially hybridizing to nucleic acids which are not of interest. Higher levels of sequence identity are preferred and include at least 75%, at least 80%, at least 85%, at least 90%, at least 95% and more preferably at least 98% sequence identity. Sequence identity can be determined using a commercially available computer program with a default setting that employs algorithms well known in the art. As used herein, sequences that have "high sequence identity" have identical nucleotides at least at about 50% of aligned nucleotide positions, preferably at least at about 60% of aligned nucleotide positions, and more preferably at least at about 75% of aligned nucleotide positions.

Oligonucleotides used as primers or probes for specifically amplifying (i.e., amplifying a particular target nucleic acid) or specifically detecting (i.e., detecting a particular target nucleic acid sequence) a target nucleic acid generally are capable of specifically hybridizing to the target nucleic acid under stringent conditions.

As used herein, the term "sample" or "test sample" may comprise biological samples, isolated nucleic acids, or isolated microorganisms. In some embodiments, a sample is obtained from a biological source (i.e., a "biological sample"), such as tissue, bodily fluid, or microorganisms collected from a subject. Sample sources include, but are not limited to, sputum (processed or unprocessed), bronchial alveolar lavage (BAL), bronchial wash (BW), blood, bodily fluids, cerebrospinal fluid (CSF), urine, plasma, serum, or tissue (e.g., biopsy material). Preferred sample sources include nasopharyngeal swabs, wound swabs, and nasal washes, and CSF. The term "patient sample" as used herein refers to a sample obtained from a human seeking diagnosis and/or treatment of a disease. In some embodiments, a sample comprises isolated nucleic acids. In some embodiments a sample comprises a crude biological sample from which nucleic acids have not been extracted. In some embodiments a sample may be a biological sample that was subjected to reverse transcription such that it comprises cDNA.

A reagent mixture comprises a sample, primers, and reagents necessary for PCR and/or reverse transcription (RT).

An "amplification master mix" or an "RT amplification master mix" comprises all the reagents (including primers) for PCR amplification and/or reverse transcription, but does not contain a sample or target nucleic acid to be amplified.

The terms "target nucleic acid" "target nucleic acid sequence" or "target sequence" as used herein refer to a sequence which includes a segment of nucleotides of interest to be amplified and detected. Copies of the target sequence which are generated during the amplification reaction are referred to as amplification products, amplimers, or amplicons. Target nucleic acid may be composed of segments of a chromosome, a complete gene with or without intergenic sequence, segments or portions of a gene with or without intergenic sequence, or sequence of nucleic acids to which probes or primers are designed. Target nucleic acids may include a wild-type sequence(s), a mutation, deletion or duplication, tandem repeat regions, a gene of interest, a region of a gene of interest or any upstream or downstream region thereof such as a 5' untranslated region (UTR). Target nucleic acids may represent alternative sequences or alleles of a particular gene. Target nucleic acids may be derived from genomic DNA, cDNA, or genomic RNA. As used herein target nucleic acid may be DNA (such as genomic DNA or cDNA) or RNA. In some embodiments, a target sequence is a viral RNA sequence and/or the cDNA equivalent thereof. In some embodiments, a target nucleic acid is an enteroviral sequence or a parechoviral sequence.

A "positive control nucleic acid" or "internal control" as used herein is a nucleic acid known to be present in a sample at a certain amount or level. In some embodiments, a positive control nucleic acid is not naturally present in a sample and is added to the sample prior to subjecting the reaction-sample mixture to real-time polymerase chain reaction in the disclosed methods for determining the presence or absence of enterovirus and/or parechovirus. As used herein, a "cycle threshold" (Ct) for an analyte is the PCR cycle at which the fluorescence signal crosses a specified fluorescence threshold. The Ct depends on the amplification reaction efficiency which includes starting template copy number, organism lysis, PCR amplification, hybridization or cleavage of fluorogenic probe and sensitivity of detection.

A "stem sequence" as used herein is a pair of self-complementary nucleotide sequences that flank a probe or probe element hybridizing nucleotide sequence. Each of the stem sequences is 4, 5, 6, 7, 8, 9 or 10 nucleotides in length. In some embodiments, a stem sequence is 6-7 nucleotides in length. Stem sequences that flank a probe element permit hairpin loop formation of the probe element.

Biological Samples and Sample Preparation

Samples in which enteroviruses and parechoviruses can be detected using the disclosed methods may be from sterile and/or non-sterile sites. Samples can be biological samples including body fluids such as whole blood, plasma, serum, cell free plasma, urine, cerebrospinal fluid (CSF), synovial fluid, pleural fluid, pericardial fluid, intraocular fluid and sputum. Typical samples are serum, plasma, throat or rectal swab in transport media, stool, and CSF. Additional suitable biological samples include tissue biopsies, stool samples, endotracheal aspirates, throat and rectal swab samples, nasopharynx samples (nasal swab). As used herein, "cell-free plasma" indicates plasma containing less than 1% cells by volume.

In some embodiments, a biological sample is suspected of containing enterovirus and/or parechovirus nucleic acids and/or it may be obtained from an individual suspected of being infected with enterovirus and/or parechovirus. In some embodiments, a sample is a biological sample that was subjected to reverse transcription so that RNA initially present in the biological sample (including enteroviral and/or parechoviral RNA if present) was reverse transcribed into cDNA. In this embodiment, the sample contains target cDNA. In some embodiments the cDNA is not extracted from the sample prior to RT-PCR or other detection assay.

Although the disclosed methods preferably employ unprocessed biological samples thus resulting in a direct, streamlined sample-to-answer process, the detection methods disclosed herein also are effective if used on isolated nucleic acid (DNA and/or RNA) purified from a biological sample according to any methods well known to those of skill in the art. If desired, the sample may be collected or concentrated by centrifugation and the like. Alternatively, a biological sample may be processed using a commercially available nucleic acid extraction kit.

Reverse Transcription and Real-Time PCR

In the present methods, the presence of enteroviral and/or parechoviral target RNA in a sample is tested by reverse transcription and polymerase chain reaction (RT-PCR). When used together, reverse transcription and polymerase chain reaction may be performed sequentially in two steps, or together in one step with all RT and PCR reaction composition reagents being added to the sample.

In a two-step method, incubation of a sample in a reverse transcription reaction composition allows a DNA copy from the target RNA to be synthesized. The RT reagent mix includes a primer that hybridizes to the target RNA to prime the synthesis of the copy DNA. In addition, the RT reagent mix includes dNTPs, $MgCl_2$, KCl, a reverse transcriptase and a reverse transcriptase buffer. More than one primer may be included if it is desired to make DNA copies from more than one target RNA. Typically, however, no RNase inhibitor is used. The product of the reverse transcription reaction optionally may then be transferred to another assay tube where PCR is performed according to protocol well known in the art. The amplification master mix typically includes a pair of primers that initiate synthesis of the desired segment of DNA from the reverse transcribed template. In addition, the amplification master mix usually comprises dNTPs, a DNA polymerase such as a thermostable DNA polymerase such as Taq polymerase, and polymerase buffer. In some embodiments, the amplification master mix further comprises a cationic surfactant. More than one pair of primers is included if synthesis of multiple target sequences is desired. Also, in some embodiments, a single new primer may be added that will amplify a DNA segment with the original RT primer as the second primer of the pair. Additional reverse transcriptases that may be used for viral samples include, but are not limited to, HIV Reverse Transcriptase (Ambion), Transcriptor Reverse Transcriptase (Roche), Thermoscript Reverse Transcriptase (Invitrogen). Additional DNA polymerases that may be used include, but are not limited to, Pfu, Vent, and Sequitherm DNA Polymerase (EPICENTRE).

In some embodiments of the method of the present invention, a biological sample is combined with an RT amplification master mix that contains DNA polymerase, reverse transcriptase, RNase inhibitor, salts, deoxynucleotides, an internal control, and probes and primers for target and internal control so that RT and PCR can be carried out in a single assay. In some embodiments, the biological sample is heated to separate the secondary structure of RNA present in the sample, and the heated sample is contacted with the RT amplification master mix to form the reaction mixture. In some embodiments, the biological sample is contacted with the RT amplification master mix to form the reaction mixture, and then the reaction mixture containing the biological sample is heated to separate the secondary structure of RNA present in the sample.

Regardless of whether the RT-PCR is carried out as two steps or one step, the RT step is run first and typically consists of a single temperature incubation. In some embodiments, the single temperature is from about 42° C. to about 60° C. Different temperatures are appropriate for different RT enzymes and different primers, as is known to one skilled in the art, and the temperature should be sufficient to permit reverse transcription of RNA into cDNA. The subsequent PCR reaction typically consists of an initial incubation at a predetermined temperature sufficient to denature the cDNA and also to activate heat activated Taq polymerase enzymes. This is then followed by multiple cycles of amplification of the cDNA target. In some embodiments, the heating and cooling cycle is repeated at least 12, 13, 14, 15, 18, 19, 20, 21, 22 or 23 times up to 15, 20, 25, 20, 25, 30, 35, 40 or more times. In some embodiments, three operations are performed during each cycle: target denaturation, primer annealing and primer extension. In some embodiments, target denaturation occurs at greater than about 90° C. Primer annealing temperature is dictated by the melting temperature of the specific primers used in the reaction and primer extension may be performed at temperatures ranging from about 56° C. to about 72° C. When primer annealing and extension are performed at the same temperature, this is a two temperature PCR compared with a three temperature PCR in which each of the three steps occur at a different temperature. After the amplification phase is complete, a final extension time is typically added to ensure the synthesis of all amplification products.

The PCR preferably is a multiplex PCR reaction. A reaction mixture can contain a primer pair directed to enterovirus and a primer pair directed to parechovirus. An internal control (IC) also can be included in the sample, utilizing oligonucleotide primers, probes and/or primer-probes.

In some embodiments, PCR and/or RT-PCR is performed in a centrifugal microfluidic disc. As used herein, a "centrifugal microfluidic disc" is a circular disc that spins on its axis within a thermal cycler and contains compartments in which a biological sample can be deposited. Exemplary centrifugal microfluidic discs are the Direct Amplification Discs (8 wells) and the Universal Disc (96 wells) from Focus Diagnostics that are utilized in conjunction with a 3M™ Integrated Cycler thermal cycler sold by 3M™. The 3M™ Integrated Cycler can receive a Universal or Direct Amplification Disc and is capable of performing multiple assays per disc. In some embodiments a biological sample is deposited in a gene rotor disc. As used herein, a "gene rotor disc" is a centrifuge rotor insert that holds tubes or other compartments that can house samples and/or sample-amplification mixtures. Examples of a gene rotor disc are the Qiagen Rotor Discs and/or Gene Discs that are utilized with the Qiagen Rotor-Gene Q thermalcycler.

Target Nucleic Acids and Primers

In accordance with the present invention, oligonucleotide primers and/or probes are used in the methods described herein to amplify and detect target enteroviral and/or parechoviral nucleic acids such as all or a portion of marker genes specific to enterovirus and/or parechovirus. In one embodiment, the method involves employing a primer pair directed to the 5' untranslated region (UTR) of the enterovirus genome and a primer pair directed to the 5' UTR of the parechovirus genome, including fragments of any or both of these regions. The enterovirus primer pair is capable of detecting and/or hybridizing to the 5' UTR of at least 64 serotypes of enterovirus. The parechovirus primer pair is capable of detecting and/or hybridizing to the 5' UTR of at least 8 seroytpes of parechovirus. In some embodiments, the enterovirus primers specifically hybridize to sequences within nucleotides 452-599 of the 5' UTR of the enterovirus genome (or the complement thereof) set forth in GenBank Accession No. KC436272. In some embodiments, the parechovirus primers specifically hybridize to sequences within positions 535-599 of the 5' UTR of the parechovirus genome (or the complement thereof) set forth in GenBank Accession No. AJ005695.

In addition, primers can also be used to amplify one or more control nucleic acid sequences.

The target nucleic acids described herein may be detected individually or in a multiplex format, utilizing individual labels for each target. In a particular embodiment, a multiplex reaction comprises a fluorescent labeled primer-probe such as a SCORPION® primer-probe used in a primer pair specifically directed to the 5' UTR of the enterovirus genome and another fluorescent labeled primer-probe such as a SCORPION® primer-probe used in a primer pair specifically directed to the 5' UTR of the parechovirus genome. In some embodiments the fluorescent label of the enterovirus primer pair is different than that of the parechovirus primer pair.

In some embodiments, a mix of primers is provided having degeneracy at one or more nucleotide positions. Degenerate primers are used in PCR where variability exists in the target nucleic acid sequence, i.e. the sequence information is polymorphic. Typically, degenerate primers will exhibit variability at no more than about 4, no more than about 3, preferably no more than about 2, and most preferably, no more than about 1 nucleotide position within the primer.

Accordingly, in some embodiments, at least one primer of each primer pair in the amplification reaction comprises a detectable moiety. The detectable moiety may be on a probe that is covalently linked to the primer, such as with a primer-probe. The probe may be detectably labeled by methods known in the art. Useful labels include, e.g., fluorophores (e.g., Cy5®, Cy3®, FITC, rhodamine, lanthamide phosphors, Texas red, a carboxyfluorescein fluorophore such as fluorescein amidite (FAM), JOE™, a xanthene dye such as Cal Fluor Red 610® ("CFR610") that fluoresces in the red region of the visible spectrum and can be effectively quenched by a quencher such as a dark Black Hole Quencher™ (BHQ™), I-BHQ2 dye, Quasar 670®, $^{32}P$, $^{35}S$, $^{3}H$, $^{14}C$, $^{121}I$, $^{131}I$ electron-dense reagents (e.g., gold), enzymes, e.g., as commonly used in an ELISA (e.g., horseradish peroxidase, beta-galactosidase, luciferase, alkaline phosphatase), colorimetric labels (e.g., colloidal gold), magnetic labels (e.g., Dynabeads™), biotin, digoxigenin, or haptens and proteins for which antisera or monoclonal antibodies are available. A fluorophore has the ability to absorb energy from light, transfer this energy internally, and emit this energy as light of a characteristic wavelength. Following the absorption of energy (a photon) from light, a fluorophore will be raised from its ground state to a higher vibrational level of an excited singlet state. In the next phase, some energy is lost as heat, returning the fluorophore to the lowest vibrational level of an excited singlet state. The lowest vibrational level of an excited singlet state is relatively stable and has a longer lifetime. From this excited singlet state, the fluorophore can return to its ground state, either by emission of light (a photon) or by a non-radiative energy transition. Light emitted from the excited singlet state is called fluorescence. Other labels include ligands or oligonucleotides capable of forming a complex with the corresponding receptor or oligonucleotide complement, respectively. The label can be directly incorporated into the nucleic acid to be detected, or it can be attached to a probe (e.g., an oligonucleotide) or antibody that hybridizes or binds to the nucleic acid to be detected.

Thus, following and/or during amplification, the enteroviral and/or parechoviral target segment amplicons can be identified, if present, by using different detectable moieties such as by size and/or color. Although the targets are referred to as "enteroviral target segment amplicon" or "parechovirus target segment amplicon" it is noted that the amplicon is actually generated from a cDNA equivalent of the viral genomic RNA sequence (so that the target amplicon is not identical to the viral RNA target sequence due to the presence of thymine instead of uracil). The detectable moiety may be a fluorescent dye. In some embodiments, the different primer pairs are labeled with different distinguishable detectable moieties. Thus, for example, CFR610 and FAM fluorescent dyes may be present on different primers in the multiplex PCR and associated with the different resulting amplicon sequences. In other embodiments, the forward primer is labeled with one detectable moiety, while the reverse primer is labeled with a different detectable moiety, e.g. FAM dye for a forward primer and HEX dye for a reverse primer. Use of different detectable moieties is useful for discriminating between amplified products which are of the same length or are very similar in length.

In some embodiments, the probe elements of the primers employed are detectably labeled and the detection is accomplished by detecting the label for each amplification product. A quencher may further be associated with the detectable label which prevents detection of the label prior to amplification of the probe element's target. SCORPION' primers comprise such probe elements.

In certain embodiments, at least one primer of each primer pair is a primer-probe. In these embodiments, the primer-probe further contains a fluorophore associated with a quencher to reduce background fluorescence. Following PCR extension with such a fluorophore labeled primer-probe, the synthesized target region is attached to the same strand as the probe. Upon denaturation, the probe portion of the primer-probe specifically hybridizes to a part of the newly produced PCR product, physically separating the fluorophore from the quencher, thereby producing a detectable signal. Thus, in some embodiments, one primer of each primer pair may be a primer-probe that comprises a probe sequence element at the 5' end of a primer, wherein the probe element further comprises a fluorophore and a quencher.

The present inventors discovered that detection of a specific region of the 5' UTR of the enterovirus genome (i.e., nucleotides 452-599 of the 5' UTR) allows detection of any of 64 serotypes of enterovirus and can distinguish a sample containing enterovirus from one that contains other viral species or strains that are not enterovirus. In addition, the present inventors discovered that detection of a specific region of the 5' UTR of the parechovirus genome (i.e., nucleotides 535-599 of the 5' UTR) allows detection of any of 8 serotypes of parechovirus and can distinguish a sample containing parechovirus from one that contains other viral species or strains that are not parechovirus.

Enterovirus Detection

The primers of a primer pair for detecting and/or amplifying enterovirus have primer elements that hybridize to regions within nucleotides 452-599 of the 5' UTR of the enterovirus genome. In some embodiments, a primer pair contains a primer with a primer element that specifically hybridizes to a nucleic acid comprising or consisting of the sequence 5'-AATTGTCACCATAAGCAGCCA-3' (SEQ ID NO:1) or its full complement. In some embodiments, one primer of a primer pair comprises or consists of a primer element sequence that is at least 90% identical to SEQ ID NO:1 or at least 90% identical to the full complement of SEQ ID NO:1 and that specifically hybridizes under stringent conditions to SEQ ID NO:1 or the full complement thereof. In some embodiments the primer element is at least 16, 17, 18, 19 nucleotides and/or up to 18, 19, 20, 22, 25, 30, 40 or 50 nucleotides long and is at least 84, 85, 86 or 90% identical to SEQ ID NO:1. The primer element may comprise or consist of at least 16, 17, 18, 19, 20 or 21 consecutive nucleotides of SEQ ID NO:1 or the full complement of SEQ ID NO:1, and hybridizes to a nucleic acid comprising or consisting of SEQ ID NO:1 or its full complement under stringent conditions.

In some embodiments, a primer pair for detecting and/or amplifying enterovirus contains a primer with a primer element that specifically hybridizes to a nucleic acid comprising or consisting of the sequence 5'-CCCCTGAATGCGGCTAATC-3' (SEQ ID NO:2) or its full complement. In some embodiments, the primer element comprises a sequence that is at least 90% identical to SEQ ID NO:2 or at least 90% identical to the full complement of SEQ ID NO:2 and that specifically hybridizes under stringent conditions to a nucleic acid comprising or consisting of SEQ ID NO:2 or its full complement. In some embodiments the primer element is at least 16, 17, 18, 19 nucleotides and/or up to 18, 19, 20, 22, 25, 30, 40 or 50 nucleotides long and is at least 84, 85, 86 or 90% identical to SEQ ID NO:2. The primer element may comprise or consist of at least 16, 17, 18, 19, 20 or 21 nucleotides of SEQ ID NO:2 or the full complement of SEQ ID NO:2, and hybridizes to a nucleic acid comprising or consisting of SEQ ID NO:2 or its full complement under stringent conditions.

In some embodiments a primer for detecting and/or amplifying enterovirus nucleic acid is a primer-probe. The primer-probe may comprise a primer element as discussed above, and a probe element comprising a nucleotide sequence at least 90% identical to SEQ ID NO:3 or at least 90% identical to the full complement of SEQ ID NO:3. In some embodiments, a probe element comprises at least 19, 20, 21, 22, 23 or 24 consecutive nucleotides of SEQ ID NO:3 or of the complement of SEQ ID NO:3. The probe element specifically hybrizes to the corresponding region of SEQ ID NO:3 or the complement of SEQ ID NO:3 under stringent hybridization conditions.

In a specific embodiment, an enterovirus primer pair contains both of the above described enterovirus primers (i.e., a primer with a primer element that specifically hybridizes to a nucleic acid comprising or consisting of SEQ ID NO:1 or its complement and a primer with a primer element that specifically hybridizes to a nucleic acid comprising or consisting of SEQ ID NO:2 or its complement).

In another specific embodiment, one primer of an enterovirus primer pair comprises or consists of SEQ ID NO:1 and the other primer of the enterovirus primer pair is a primer-probe that comprises or consists of (from the 5' to 3' direction) a quencher moiety linked to a nucleotide sequence consisting of a first stem sequence followed by ACACG-GACACCCAAAGTAGTCGGT (SEQ ID NO:3) and a second stem sequence that is complementary to the first stem sequence, linked at its 3' end to a fluorophore and a nucleotide spacer that is a 10, 14, 15, 16, 17, 18, 19, 20, 21 or 25 atom polyethylene glycol-based linker followed by SEQ ID NO:2.

A specific enterovirus primer pair consists of:

```
Enterovirus Primer 1:
                                    (SEQ ID NO: 1)
5'd AATTGTCACCATAAGCAGCCA 3'

Enterovirus Primer 2 (a primer-probe):
                                    (SEQ ID NO: 7)
5'd BHQ-1-agcgcACACGGACACCCAAAGTAGTCGGTgcgct-FAM- Spacer18-CCCCTGAATGCGGCTAATC 3'
``` wherein "BHQ-1" is a black hole quencher moiety, the underlined sequences are self-complementary stem sequences, "FAM" is fluorescein amidite, and "Spacer18" is a spacer containing an 18 atom hexaethylene glycol linker.

Parechovirus Detection

The primers of a primer pair for detecting and/or amplifying parechovirus contain primer elements that hybridize to regions within nucleotides 535-599 of the 5' UTR of the parechovirus genome. In some embodiments, one primer of a primer pair comprises or consists of a primer element sequence that is at least 90% identical to 5' GTTGTAAGGC-CCACGAA 3' (SEQ ID NO:4) or at least 90% identical to the full complement of SEQ ID NO:4 and that specifically hybridizes under stringent conditions to SEQ ID NO:4 or the full complement thereof. In some embodiments the primer element is at least 16, 17, 18, 19 bases and/or up to 18, 19, 20, 22, 25, 30, 40 or 50 long and is at least 84, 85, 86 or 90% identical to SEQ ID NO:4. The primer element may comprise or consist of at least 16, 17, 18, 19, 20 or 21 consecutive nucleotides of SEQ ID NO:4 or the full complement of SEQ ID NO:4, and hybridizes to SEQ ID NO:4 or its full complement under stringent conditions.

In some embodiments, a primer pair for detecting and/or amplifying parechovirus contains a primer with a primer element that specifically hybridizes to a nucleic acid comprising or consisting of the sequence 5'-TCAGATC-CATAGTGTCICTTGTTA-3' (SEQ ID NO:5) or its full complement. In some embodiments, the primer element comprises a sequence that is at least 90% identical to SEQ ID NO:5 or at least 90% identical to the full complement of SEQ ID NO:5 and that specifically hybridizes under stringent conditions to SEQ ID NO:5 or its full complement. In some embodiments the primer element is at least 16, 17, 18, 19 nucleotides and/or up to 18, 19, 20, 22, 25, 30, 40 or 50 nucleotides long and is at least 84, 85, 86 or 90% identical to SEQ ID NO:5. The primer element may comprise or consist of at least 16, 17, 18, 19, 20 or 21 nucleotides of SEQ ID NO:5 or the full complement of SEQ ID NO:5, and hybridizes to SEQ ID NO:5 or its full complement under stringent conditions.

In some embodiments a primer for detecting and/or amplifying parechovirus nucleic acid is a primer-probe. The primer-probe may comprise a primer element sequence (discussed above) and a probe element comprising a nucleotide sequence at least 90% identical to 5'-ATGCCCA-GAAGGTACCCG-3' (SEQ ID NO:6) or at least 90% identical to the full complement of SEQ ID NO:6. In some embodiments, a probe element comprises 19, 20, 21, 22, 23 or 24 consecutive nucleotides of SEQ ID NO:6 or of the complement of SEQ ID NO:6. The probe element specifically hybrizes to the corresponding region of SEQ ID NO:6 of the complement of SEQ ID NO:6 under stringent hybridization conditions.

In a specific embodiment, a parechovirus primer pair contains both of the above described parechovirus primers (i.e., a primer with a primer element that specifically hybridizes to a nucleic acid comprising or consisting of SEQ ID NO:4 or its complement and a primer with a primer element that specifically hybridizes to a nucleic acid comprising or consisting of SEQ ID NO:5 or its complement).

In another specific embodiment, one primer of an parechovirus primer pair comprises or consists of SEQ ID NO:4 and the other primer of the parechovirus primer pair is a primer-probe that comprises or consists of (from 5' to 3') a fluorophore linked to a nucleotide sequence consisting of a first stem sequence followed by SEQ ID NO:5 and a second stem sequence that is complementary to the first stem sequence, linked at its 3' end to a quencher and a spacer that is a 10, 14, 15, 16, 17, 18, 19, 20, 21 or 25 atom polyethylene glycol linker followed by SEQ ID NO:6.

A specific parechovirus primer pair consists of:

```
Parechovirus Primer 1:
                                    (SEQ ID NO: 4)
5'd GTTGTAAGGCCCACGAA 3'

Parechovirus primer 2 (a primer-probe):
                                    (SEQ ID NO: 8)
5'd CFR610- cgcgcgATGCCCAGAAGGTACCCGcgcg-BHQ-2-Spacer 18-

TCAGATCCATAGTGTCICTTGTTA 3'
``` wherein "CFR610" is the xanthene dye Cal Fluor Red 610®, the boxed sequences are self-complementary stem sequences, "BHQ-2" is a black hole quencher and "Spacer18" is a spacer containing an 18 atom hexaethyleneglycol linker.

The present inventors discovered that the above primer pairs surprisingly outperformed other primer pairs in a multiplexed, direct amplification reaction in human biological samples and were able to detect 64 serotypes of enterovirus as well as parechovirus serotypes 1-8.

Product Detection

The disclosed methods for determining the presence or absence of an enterovirus and/or parechovirus in a sample involve, among other steps, determining if an enteroviral or a parechoviral nucleotide sequence is amplified in a sample. The determining step may be performed during and/or after PCR amplification. In some embodiments, at least one primer of each primer pair (i.e., the primer pair directed to enterovirus and the primer pair directed to parechovirus) is a primer-probe and generates a fluorescent signal during PCR amplification. The signal is detected for the enterovirus sequence amplification and/or parechovirus sequence amplification, thus indicating that the virus(es) is/are present in the sample.

Real-time PCR methods, which do not require a preparation step prior to detection of the amplified product, are preferably used in the present invention. Most real-time methods detect amplified product formation by monitoring changes in fluorescence during thermocycling. In some embodiments, a different fluorescent signal is generated for the parechovirus sequence amplification versus the enterovirus sequence amplification, thus allowing the observer to distinguish between the two viruses.

A detectably labeled primer-probe can be used for real-time PCR. Suitable detectable labels for primer-probes such as SCORPION® primer-probes include fluorophores such as fluorescein bioconjugates and amine-reactive succinimidyl esters of carboxyfluorescein (commonly called FAM). A primer-probe also contains a quencher. In the absence of the target, the quencher nearly absorbs the fluorescence emitted by the fluorophore. During the Scorpion PCR reaction, in the presence of the target, the fluorophore and the quencher separate which leads to an increase in the fluorescence emitted. The fluorescence can be detected and measured in the reaction tube. Suitable quenchers include the Black Hole Quencher® (BHQ®, Biosearch Technologies). Dark quenchers, such as DABCYL, are dyes with no native fluorescence. The BHQ dyes are true dark quenchers with no native emission due to their polyaromatic-azo backbone. Substituting electron-donating and—withdrawing groups on the aromatic rings produces a complete series of quenchers with broad absorption curves that span the visible spectrum: BHQ-0 (493 nm), BHQ-1 (534 nm), BHQ-2 (579 nm) and BHQ-3 (672 nm). These quenchers can be paired with all common reporter dyes to construct efficiently quenched qPCR probes for multiplexing assays. In addition to quenching by FRET, BHQ dyes have also been shown to efficiently quench fluorescence through static quenching via formation of a ground state complex with the reporter dye. Other fluorophores and quenchers with various absorption and emission values are known in the art.

EXAMPLES

The present methods, thus generally described, will be understood more readily by reference to the following examples, which are provided by way of illustration and are not intended to be limiting of the present methods and kits.

Example 1

A panel of clinical cerebrospinal fluid (CSF) samples or contrived panels of synthetic CSF were tested and the results were compared to real-time PCR results to determine clinical performance of the Simplexa Enterovirus and Parechovirus Direct assay as compared to that of real-time PCR methods that utilize conventional nucleic acid extraction.

Simplexa Direct Assay:

Simplexa Direct kits (Focus Diagnostics, Cypress, Calif.) contain all reagents for on-board extraction and real-time PCR. For each reaction on the Direct Amplification Disc, unprocessed CSF sample was loaded directly into a sample well of one wedge of the Disc without any sample preparation steps. Amplification reaction mix was pipetted into a reaction well of the wedge, wherein the amplification reaction mix contained, Enterovirus primers 1 and 2 and Parechovirus primers 1 and 2 as described below:

```
Enterovirus Primer 1:
                                        (SEQ ID NO: 1)
5'd AATTGTCACCATAAGCAGCCA 3'

Enterovirus Primer 2 (a primer-probe):
                                        (SEQ ID NO: 7)
5'd BHQ-1-agcgcACACGGACACCCAAAGTAGTCGGTgcgct-FAM- Spacer18-CCCCTGAATGCGGCTAATC 3'

Parechovirus Primer 1:
                                        (SEQ ID NO: 4)
5'd GTTGTAAGGCCCACGAA 3'

Parechovirus primer 2 (a primer-probe):
                                        (SEQ ID NO: 8)
5'd CFR610-cgcgcgATGCCCAGAAGGTACCCGcgcg-BHQ-2-

Spacer 18-TCAGATCCATAGTGTCICTTGTTA 3'
```

The reaction mix further contained DNA polymerase, reverse transcriptase, RNase inhibitor, salts, deoxynucleotides, an internal control, and probes and primers for internal control. The wedge was sealed with foil and the Direct Amplification Disc was then inserted into a 3M™ Integrated Cycler (3M, St. Paul, Minn., USA) and reverse transcription and real time PCR commenced in the cycler. The PCR cycling conditions include the following steps: i) sample pre-heat at 75° C., 180 seconds, 1 cycle ii) reverse transcription at 50° C., 720 seconds, 1 cycle, iii) polymerase activation at 97° C., 120 seconds, 1 cycle iv) denaturation at 97° C., 10 seconds and annealing/extension/detection at 56° C., 10 seconds and 58° C., 30 seconds for 45 cycles. Target DNA (derived from enteroviral and/or parechoviral genomic RNA) was specifically amplified and simultaneously detected by fluorescent-labeled primer-probes in the same reaction. Data collection and analysis were performed with Integrated Cycler Studio software.

Viral Strains:

The following strains were used in the LoD studies: CVA1, CVA17, and CVA9, and parechovirus HPEV-1 and HPEV-3 (ZeptoMetrix, Buffalo, N.Y.). The following parechovirus strains were used in the specificity study: HPEV1, HPEV2, HPEV3, HPEV4, HPEV5, and HPEV6 (ZeptoMetrix, Buffalo, N.Y.).

Limit of Detection (LoD) Studies:

LoD studies were performed to determine the analytical sensitivity of the assays. The presumptive LoD for each viral stock was determined as the lowest concentration with 4/4 replicate detected in synthetic CSF (Golden West Biologicals, Temecula, Calif.).

Sensitivity and Specificity Studies:

Clinical performance of the Simplexa Enterovirus and Parechovirus Direct assay was evaluated using a panel of 154 CSF samples comprising of 7 Parechovirus positives, 74 enterovirus positives and 74 Parechovirus/Enterovirus negatives, as reported by a real-time PCR assay. Additionally a panel of 24 Parechovirus positive samples contrived in synthetic CSF was used. The contrived panel was made using quantified viral stocks of parechovirus serotypes 1-6 at 10×, 4×, 2× and 1× concentration of Simplexa LoD.

Cross-Reactivity Studies:

Cross-reactivity was evaluated using a diverse panel of bacteria and viruses. A panel of organisms, infection with which may present similar clinical symptoms as enterovirus and/or parechovirus infection, was used to determine cross-reactivity. The panel consisted of $10^6$ CFU/mL of bacteria or $10^5$ TCID$_{50}$/ml of virus in synthetic CSF.

Results:

LoD: The LoD studies using synthetic CSF showed that Simplexa Enterovirus and Parechovirus Direct detected enterovirus and parechovirus strains at <1×10$^3$ TCID$_{50}$/mL. The positive and negative agreements for Simplexa Enterovirus and Parechovirus Direct as compared to a real-time PCR assay which uses a conventional extraction procedure were 95.6% (65/68) and 89% (65/73) for enterovirus and 92.6% (25/27) and 92.2% (71/77) for Parechovirus respectively.

TABLE 1

Limit of Detection for Enterovirus and Parechovirus Strains

| Strain | LoD (TCID50/ml) | Mean Ct | Min Ct | Min Ct | Replicates detected |
|---|---|---|---|---|---|
| CVA1 | 20.8 | 35.7 | 34.8 | 36.5 | 4/4 |
| CVA17 | 6.5 | 40.1 | 39.3 | 40.9 | 4/4 |
| CVA9 | 104 | 39.3 | 36.9 | 42.3 | 4/4 |
| HPEV-1 | 744 | 40.4 | 39.2 | 42.5 | 4/4 |
| HPEV-3 | 9.3 | 41.1 | 39.3 | 42.4 | 4/4 |

Simplexa Enterovirus and Parechovirus Direct Relative Positive and Negative Agreements are as listed in Tables 2 and 3.

TABLE 2

Enterovirus Concordance for CSF Samples

| | Previous results | | |
|---|---|---|---|
| Simplexa ™ | EV Positive | EV Negative | Total |
| Enterovirus Positive | 65 | 8# | 73 |
| Enterovirus Negative | 9* | 65 | 74 |
| Total | 74 | 73 | 147 |
| % Positive agreement | | 87.8% (65/74) | |
| % Negative agreement | | 89% (65/73) | |

*9/65 CSF samples previously reported as enterovirus positive were Simplexa negative. 6 of these samples were negative on repeat testing with real-time PCR. As a result, the positive agreement increased to 95.6% (65/68)
8/65 CSF samples previously reported as enterovirus negative were Simplexa positive.

TABLE 3

Parechovirus Concordance for CSF Samples

| | Previous results | | |
|---|---|---|---|
| Simplexa ™ | HPEV Positive | HPEV Negative | Total |
| Parechovirus Positive | 25 | 6#a | 31 |
| Parechovirus Negative | 2* | 71 | 73 |
| Total | 27 | 77 | 104 |
| % Positive agreement | | 92.6% (25/27) | |
| % Negative agreement | | 92.2% (71/77) | |

*2/7 CSF samples previously reported as parechovirus positive was Simplexa negative. One of the samples was negative on repeat testing with real-time PCR.
4 of the contrived parechovirus positive samples was negative with the real-time PCR assay.
a2/73 CSF samples previously reported as negative was Simplexa positive. One of the samples was negative on repeat testing with real-time PCR.

Cross-Reactivity:
No cross-reactivity to pathogens in Table 4 was detected.

TABLE 4

Cross-Reactivity Pathogens Tested in Synthetic CSF

| | | |
|---|---|---|
| Adenovirus 2 | Epstein Barr virus (EBV) | Mumps |
| Citrobacter fruendii | Herpes simplex virus (HSV) 1 | Parainfluenza 1 |
| Citrobacter koseri | Herpes simplex virus (HSV) 2 | Parainfluenza 2 |
| Escherichia coli | Human Herpes virus (HHV) 6 | Parainfluenza 3 |
| Haemophilus influenzae | Human Herpes virus (HHV) 7 | Parainfluenza 4 |
| Haemophilus parainfluenza | Human Herpes virus (HHV) 8 | Varicella Zoster virus (VZV) |
| Streptococcus agalactiae (GBS) | Influenza A | intact Whole blood cells |
| Neisseria meningitides | Influenza B | RNA from Whole blood cells |
| Cytomegalovirus (CMV) | Measles | |

The ability to detect selected enterovirus types was further confirmed in a follow-up study. The exemplary enterovirus types detected in the follow-up study using the Simplexa Enterovirus and Parechovirus Direct assay are shown in Table 5.

TABLE 5

Selected Enterovirus Strains Detected in Follow-up Study

| Enterovirus strains | Source | Results |
|---|---|---|
| Coxsackievirus A 5 | ATCC | Detected |
| Coxsackievirus A 6 | ATCC | Detected |
| Coxsackievirus A 9 | ATCC | Detected |
| Coxsackievirus A 10 | ATCC | Detected |
| Coxsackievirus A 11 | ATCC | Detected |
| Coxsackievirus A 13 | ATCC | Detected |
| Coxsackievirus A 17 | ATCC | Detected |
| Coxsackievirus A 19 | ATCC | Detected |
| Coxsackievirus A 24 | ATCC | Detected |
| Coxsackievirus B 1 | ATCC | Detected |
| Coxsackievirus B 2 | ATCC | Detected |
| Coxsackievirus B 4 | ATCC | Detected |
| Coxsackievirus B 5 | ATCC | Detected |
| Coxsackievirus B 6 | ATCC | Detected |
| Echovirus 1 | ATCC | Detected |
| Echovirus 11 | ATCC | Detected |
| Echovirus 12 | ATCC | Detected |
| Echovirus 13 | ATCC | Detected |
| Echovirus 18 | ATCC | Detected |
| Echovirus 19 | ATCC | Detected |
| Echovirus 25 | ATCC | Detected |
| Echovirus 26 | ATCC | Detected |
| Echovirus 29 | ATCC | Detected |
| Echovirus 30 | ATCC | Detected |
| Echovirus 31 | ATCC | Detected |
| Echovirus 4 | ATCC | Detected |
| Echovirus 6 | ATCC | Detected |
| Echovirus 7 | ATCC | Detected |
| Echovirus 9 | ATCC | Detected |
| Enterovirus 68 | ATCC | Detected |
| Enterovirus 70 | ATCC | Detected |
| Enterovirus 71 | ATCC | Detected |

CONCLUSIONS

Simplexa Enterovirus and Parechovirus Direct was capable of directly detecting and differentiating enterovirus and parechovirus from un-extracted CSF samples, with a performance comparable to that of the conventional PCR assay that employs nucleic acid extraction. By targeting the 5' UTR of enterovirus and the 5' UTR of parechovirus, 64 serotypes of enterovirus as well as serotypes 1-6 in human CSF were effectively detected in this rapid "sample-to-answer" assay. HPEV7 and HPEV8 are not commercially available for testing, but in silico analysis shows that these serotypes can be detected. Performance of the Simplexa Enterovirus and Parechovirus Direct assay in a centrifugal microfluidic disc using an integrated thermalcycler that was capable of accommodating the disc, provided a compact system for rapid detection of enteroviruses and parechoviruses directly from human biological samples.

Unless otherwise defined, all technical and scientific terms used herein have the same meaning as commonly understood by one of ordinary skill in the art to which this invention belongs.

The inventions illustratively described herein may suitably be practiced in the absence of any element or elements, limitation or limitations, not specifically disclosed herein. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

Thus, it should be understood that although the present invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

Other embodiments are set forth within the following claims.

The invention claimed is:

1. A method for determining the presence or absence of an enterovirus and/or a parechovirus in a sample, the method comprising:
   (a) amplifying enteroviral nucleic acids, if present in the sample, with at least one first set of primers, wherein the first set of primers comprises: (i) a first primer comprising SEQ ID NO: 1, (ii) a second primer comprising SEQ ID NO:2, and (iii) a probe comprising SEQ ID NO:3; and/or
   (b) amplifying parechoviral nucleic acids, if present in the sample, with at least one second set of primers, wherein the second set of primers comprises: (i) a first primer comprising SEQ ID NO:4, (ii) a second primer comprising SEQ ID NO: 5, and (iii) a probe comprising SEQ ID NO:6.

2. The method of claim 1, wherein the probe comprising SEQ ID NO:3 comprises a quencher dye and a fluorophore.

3. The method of claim 1, wherein the probe comprising SEQ ID NO:6 comprises a quencher dye and a fluorophore.

4. The method of claim 1, wherein the sample is a biological sample selected from the group consisting of cerebrospinal fluid, blood, stool, throat swab, rectal swab, nasopharynx swab, plasma, serum and urine.

5. The method of claim 4, wherein nucleic acids are not extracted from the biological sample.

* * * * *